(12) United States Patent
Sugano et al.

(10) Patent No.: US 11,936,918 B2
(45) Date of Patent: Mar. 19, 2024

(54) MEDICAL VIDEO PROCESSING SYSTEM AND ENCODER

(71) Applicant: Medi Plus Inc., Tokyo (JP)

(72) Inventors: Naoya Sugano, Tokyo (JP); Minsu Kwon, Tokyo (JP)

(73) Assignee: MEDI PLUS INC., Tokyo (JP)

( * ) Notice: Subject to any disclaimer, the term of this patent is extended or adjusted under 35 U.S.C. 154(b) by 35 days.

(21) Appl. No.: 17/797,777

(22) PCT Filed: Feb. 5, 2021

(86) PCT No.: PCT/JP2021/004330
§ 371 (c)(1),
(2) Date: Aug. 5, 2022

(87) PCT Pub. No.: WO2021/157697
PCT Pub. Date: Aug. 12, 2021

(65) Prior Publication Data
US 2022/0408118 A1  Dec. 22, 2022

(30) Foreign Application Priority Data

Feb. 6, 2020  (JP) .................................. 2020-018659

(51) Int. Cl.
| | |
|---|---|
| *H04N 19/86* | (2014.01) |
| *A61B 90/00* | (2016.01) |
| *H04N 5/268* | (2006.01) |
| *H04N 5/91* | (2006.01) |
| *H04N 7/18* | (2006.01) |

(Continued)

(52) U.S. Cl.
CPC ............. *H04N 19/86* (2014.11); *A61B 90/37* (2016.02); *H04N 5/268* (2013.01); *H04N 5/91* (2013.01); *H04N 7/18* (2013.01); *H04N 19/162* (2014.11); *H04N 21/2187* (2013.01); *H04N 21/231* (2013.01)

(58) Field of Classification Search
None
See application file for complete search history.

(56) References Cited

U.S. PATENT DOCUMENTS

| 11,341,999 B2 | 5/2022 | Sugano et al. |
| 2014/0375768 A1 | 12/2014 | Tsuchiya et al. |

(Continued)

FOREIGN PATENT DOCUMENTS

| JP | 2016-58975 A | 4/2016 |
| JP | 2017-213181 A | 12/2017 |

(Continued)

OTHER PUBLICATIONS

International Search Report dated Apr. 6, 2021, issued in counterpart International Application No. PCT/JP2021/004330, w/English translation (5 pages).

(Continued)

*Primary Examiner* — Omar S Parra
(74) *Attorney, Agent, or Firm* — WHDA, LLP

(57) ABSTRACT

Provided is a medical video processing system capable of moderating changes in image quality of medical video resulted from encoding, and, an encoder used for the medical video system. A medical video system 1000 has a monitor group 300 and an encoder 400 that accept medical video input from a switches 100 through separate transmission paths, and the encoder 400 subjects the input medical video to encoding as well as image quality adjustment.

5 Claims, 3 Drawing Sheets

(51) Int. Cl.
  *H04N 19/162* (2014.01)
  *H04N 21/2187* (2011.01)
  *H04N 21/231* (2011.01)

(56) References Cited

U.S. PATENT DOCUMENTS

2019/0289344 A1    9/2019  Ichikawa et al.
2021/0385391 A1   12/2021  Sugano et al.

FOREIGN PATENT DOCUMENTS

| JP | 6369706 B1 | 8/2018 |
| JP | 6440136 B1 | 12/2018 |
| WO | 2014/103879 A1 | 7/2014 |
| WO | 2018/087976 A1 | 5/2018 |

OTHER PUBLICATIONS

Notice of Reasons for Refusal dated Nov. 4, 2020, issued in counterpart JP Patent Application No. 2020-018659, w/English machine translation (9 pages).
Decision to Grant a Patent dated Mar. 9, 2021, issued in counterpart JP Patent Application No. 2020-018659, w/English machine translation (6 pages).

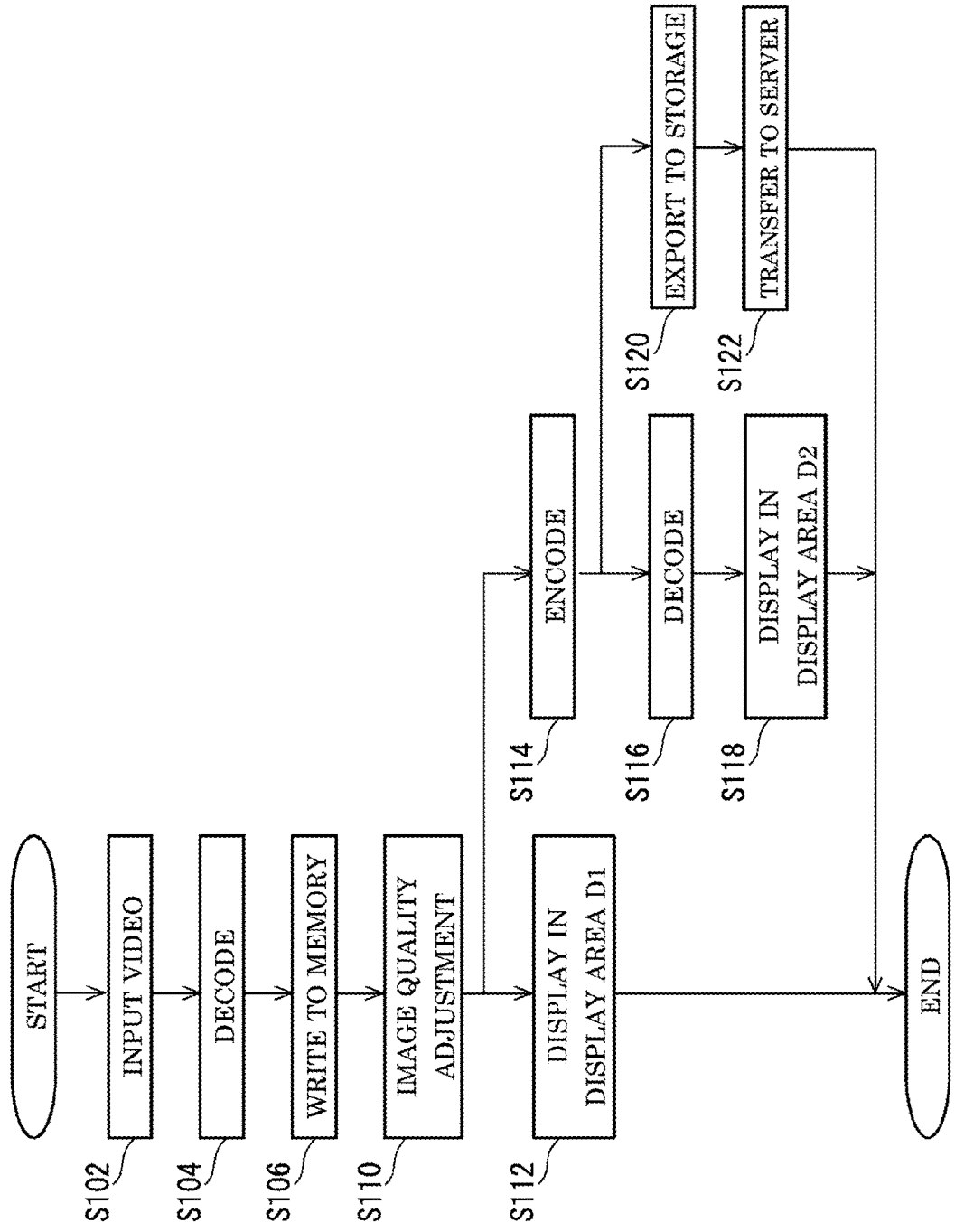

MEDICAL VIDEO PROCESSING SYSTEM AND ENCODER

TECHNICAL FIELD

The present invention relates to a medical video processing system, and an encoder used for the medical video processing system.

BACKGROUND ART

Recent medical surgery has been widely practiced referring to video of surgical field and measured results of vital signs, which are displayed on a plurality of monitors installed in an operating room or recorded on a recorder.

The present inventors have proposed a system for processing this sort of medical video, and have filed a patent application as described in Patent Literature 1.

Patent Literature 1 is aimed to enable synchronous display of medical videos captured by a plurality of cameras, and to enable edition (clipping of a part of capture period, addition of comment at a desired time point, etc.) of the medical video being synchronously displayed.

CITATION LIST

Patent Literature

[Patent Literature 1] JP 639706 B1

SUMMARY OF THE INVENTION

Technical Problem

Patent Literature 1 describes an encoder that encodes the medical video before being transferred to a server, and stored therein.

The encoding of the medical video by the encoder has, however, occasionally changed image quality of the medical video (medical video after encoded) to be stored in the server, whose impression could be different from the medical video (medical video before encoded) having been confirmed on a monitor during surgical operation, raising an issue to be solved.

The present invention, aimed at solving the aforementioned issue, is to provide a medical video processing system capable of moderating changes in the image quality of medical video resulted from encoding, and, an encoder used for the medical video system.

Solution to Problem

According to the present invention, there is provided a medical video processing system that processes medical video produced by a medical device, the system includes: a monitor accepting the medical video input through a first transmission path, and displaying thereon the input medical video; and an encoder accepting the medical video through a second transmission path which is different from the first transmission path, and subjecting the input medical video to encoding and image quality adjustment, the encoder includes: an operation accepting unit capable of accepting a user's operation for the image quality adjustment; an image quality adjusting unit that takes part in the image quality adjustment, in response to the user's operation accepted by the operation accepting unit; a recording unit that records the medical video having gone through the image quality adjustment and the encoding; and a first display area that displays the medical video having gone through the image quality adjustment, but not through the encoding, and, the system being devised so that, upon acceptance of the user's operation by the operation accepting unit during recording by the recording unit, the medical video to be displayed in the first display area is switched to a video that reflects the image quality adjustment in response to the user's operation, from the time point of acceptance of the user's operation.

There is also provided an encoder used for the medical video processing system.

According to the present invention, since the encoder, which accepts input of the medical video through the transmission path (second transmission path) different from the transmission path (first transmission path) for the medical video to be displayed on the monitor, has an image quality adjusting function, so that changes in the image quality may be moderated by preliminarily (before stored in the server) carrying out image adjustment, while considering possible changes in the image quality as a result of encoding.

With the encoder provided with the first display area, the user can adjust image quality while viewing the medical video whose image quality has not been affected by encoding, and can therefore confum an exact effect of the image quality adjustment.

Advantageous Effects of Invention

According to the present invention, there is provided a medical video processing system capable of moderating changes in the image quality of medical video resulted from encoding, and, an encoder used for the medical video system.

BRIEF DESCRIPTION OF DRAWINGS

FIG. 3 is a flow chart illustrating a process flow executed by the encoder.

DESCRIPTION OF EMBODIMENTS

Embodiments of the present invention will be explained below referring to the attached drawings. Note that all similar constituents in all drawings will be given same reference signs, so as to suitably avoid redundant explanation.

<Constituents Contained in Medical Video System 1000>

Figure 1:
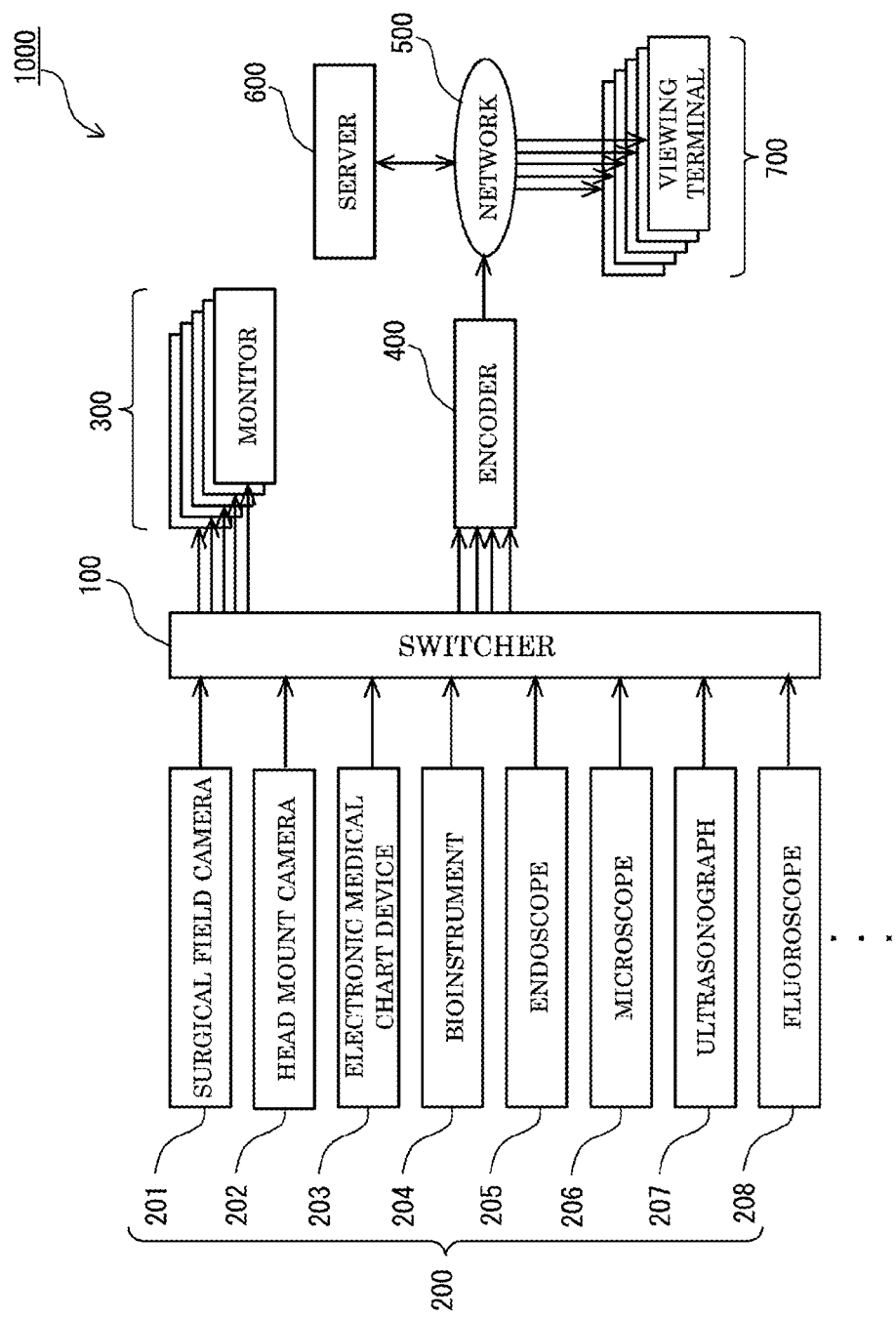
FIG. 1 is a configuration diagram illustrating a configuration of a medical video system of this embodiment.

First, the individual constituents contained in a medical video system 1000 will be explained referring to FIG. 1. FIG. 1 is configuration diagram illustrating a configuration of the medical video system 1000 of this embodiment.

Arrows illustrated in FIG. 1 represent origins and destinations of video transferred among the individual constituents. Transfer of information and data other than video does not always necessarily coincide with indication of each arrow.

A medical video system 1000 of this embodiment (the medical video system of the present invention) is an article that processes medical video produced by a medical device group 200 (the medical device of the present invention).

The medical video system 1000 has at least a monitor group 300 (the monitor of the present invention), and an encoder 400 (the encoder the present invention).

The monitor group 300 accepts the medical video input through a first transmission path, and displays thereon the input medical video.

Meanwhile, the encoder 400 accepts the medical video through a second transmission path which is different from the first transmission path, and uniquely subjects the input medical video to encoding, and concurrently subjects the input medical data to image quality adjustment.

In the medical video system 1000, the encoder having the image quality adjusting function can carry out the image quality adjustment of the medical video before stored in the server 600, while considering possible changes in the image quality as a result of encoding, thus making it possible to moderating the changes in the image quality.

From another point of view, devices on the upstream side of the encoder 400 (the medical device group 200 or a switcher 100) may otherwise have the image quality adjusting function. These devices are, however, considered to be unable to moderate the changes in the image quality even if provided with such image quality adjusting function, since both the medical video displayed on the monitor group 300 (medical video before encoded) and the medical video stored in the server 600 (medical video after encoded) are affected by the image quality adjustment.

Meanwhile, devices on the downstream side of the encoder 400 (the server 600 or a viewing terminal group 700) may otherwise have the image quality adjusting function. These devices are, however, installed remotely beyond a network 500 (outside an operating room), and are difficult to carry out the image quality adjustment at the surgeon's will, even if given with the image quality adjusting function. Hence, presupposing that the medical video is typically used for reviewing (at a conference, for example) after the surgical operation, the aforementioned system configuration is not convenient.

The medical video system 1000 of this embodiment will be specifically explained below.

The medical video system 1000 has the switcher 100; the medical device group 200 connected to input channels of the switcher 100; and the monitor group 300 and the encoder 400 individually connected to output channels of the switcher 100. The medical video system 1000 also has the server 600 that downloads and then stores video supplied from the encoder 400 through the network 500; and the viewing terminal group 700 that requests video to the server 600 through the network 500, and displays (playback) the requested video streamed through the network 500 from the server 600.

The switcher 100 is a device that receives the medical video through any of a plurality of input channels (medical device group 200), and outputs the medical video through any of a plurality of output channels which is connected to the input channel.

The medical device group 200 in this embodiment is specifically exemplified by a surgical field camera 201, a head mount camera 202, an electronic medical chart device 203, a bioinstrument 204, an endoscope 205, a microscope 206, an ultrasonograph 207, and a fluoroscope 208.

The surgical field camera 201 is a camera which shoots a surgical field at a position confronted to the surgical field, and then outputs the recorded video to the switcher 100.

The head mount camera 202 is a camera set on the head of an operator (surgeon), and outputs the recorded video to the switcher 100.

The electronic medical chart device 203 is a computer device which stores medical chart (medical record) of a subject (patient), and outputs the stored medical chart to the switcher 100. In this embodiment, not only a single medical chart, but also a plurality of medical charts may be output from the electronic medical chart device 203. The electronic medical chart device 203, when outputting a plurality of medical charts, can output the medical charts while dividing them so as to be directed to every input channel of the switcher 100.

The bioinstrument 204 is a measurement instrument which measures vital sighs (blood pressure, pulse rate, electrocardiogram, breathing rate, body temperature, etc.) of the subject, and outputs the measured vital signs to the switcher 100.

The endoscope 205 is a medical device that has a lens of camera, a forceps hole and so forth mounted on the front end of a tube to be inserted into the body of subject, and outputs video captured by using the camera to the switcher 100.

The microscope 206 is a medical device that magnifies a very small part (nerve, blood vessel and so forth of the subject) up to a size visible to the naked eyes, and displays and captures such part, and is capable of outputting the magnified captured video to the switcher 100.

The ultrasonograph 207 is a medical device that applies ultrasonic wave to a target (thoracic, abdomen and so forth of the subject) and visualizes the reflection, which is also called "echo". The ultrasonograph 207 can output the video generated from the reflected ultrasonic wave to the switcher 100.

The fluoroscope 208 is a medical device that irradiates X-ray to a target (the subject), produces X-ray image on the basis of transmitted X-ray, and can output the produced X-ray image to the switcher 100.

The medical device group 200 exemplified here is merely a specific example, where embodiments of the present invention may lack a part of these components, or may contain any other medical device having not been mentioned above.

Note that video data regarding video and so forth, produced in the present embodiment by the medical device group 200 (including medical record and measured results of vital signs), and video that is displayed on a device having such video data entered therein (monitor group 300 and viewing terminal group 700 described later) and so forth, are considered to fall in the category of "medical video", and will be described below.

The monitor group 300 includes display devices that receive medical video output from the medical device group 200, and displays the received medical video.

Note that the number of display devices that configure the monitor group 300 is not specifically limited, so that even a single display device is also acceptable.

The encoder 400 receives the medical video which is output from the medical device group 200 through the switcher 100, and subjects the received medical video to the encoding and the image quality adjustment, so as to covert the format suitable for transfer to, and storage in the server 600.

Note that the encoder of the present invention may only function to receive the medical video, and to subject the received medical video to the encoding and the image quality adjustment, but may have other function. Hence, the encoder of the present invention is not always necessarily specialized to these functions. For example, the encoder 400 may have a recording function that enables recording of the medical video in a built-in unillustrated storage, a playback function that enables playback of the medical video stored in the storage, or a capture function that clips each frame composing the medical video to produce a still picture.

The encoder 400 in this embodiment has four input systems, can receive the medical video through each of four output channels of the switcher 100, can encode the individual medical video, and can store them in the server 600.

Note that the number of input systems of the encoder 400 is not specifically limited, and may be smaller or larger than four.

The encoder 400 can also subject the input medical video to the image quality adjustment. More specifically, the encoder 400 accepts a user's operation, and carries out the image quality adjustment in response to the accepted operation. The user can therefore store the medical video, with the image quality adjusted as desired, in the server 600.

The user's operation, and the image quality adjustment in response to the operation will be descried later.

Note that the encoder 400 of this embodiment will be explained on the premise that it has the image quality adjusting function in response to the user's operation, without denying an embodiment that the encoder has the image quality adjusting function without accepting the user's operation.

The encoder 400 has four input systems, and can receive the medical video through each of four output channels of the switcher 100.

The encoder 400 can subject each medical video accepted from each input system to the encoding and the image quality adjustment. Now, the encoder 400 does not always necessarily carry out the image quality adjustment for all input systems, but instead may only carry out the image quality adjustment in response to the user's operation.

Note that the number of input systems of the encoder 400 is not specifically limited, and may be smaller or larger than four.

The network 500 may be configured by various computer networks such as the Internet, local area network (LAN) and so forth, or combinations of them. Connection for communication among the individual components contained in the network may be any of wired communication, wireless communication, or combination of them.

The server 600 can store the medical video transferred from the encoder 400.

To the viewing terminal group 700, the server 600 can selectively provide streaming (streaming of already captured medical video), or live streaming (streaming of medical video while concurrently captured).

The medical video system 1000, although having only one server 600 as illustrated in FIG. 1, may alternatively have a plurality of servers 600. For example, the medical video system 1000 may be constructed with a server 600 for on-demand streaming, and a separate server 600 for live streaming.

The viewing terminal group 700 is computer equipment having the right to access the server 600, and can request display (playback) of medical video data stored in the server 600, depending on the access right. The server 600 distributes the requested video through the network 500, in response to the request for display issued by the viewing terminal group 700 (either by on-demand streaming or by live streaming).

In the medical video system 1000 of this embodiment illustrated in FIG. 1, there are a transmission path of the Medical video from the medical device group 200 to the monitor group 300, and a transmission path of the medical video from the medical device group 200 to the encoder 400, which are separated by the switcher 100.

Hence, the monitor group 300 and the encoder 400 receive the medical video, individually through different transmission paths (the first transmission path and the second transmission path, in the present invention).

The monitor group 300 is understood to be an article that displays thereon the input medical video. Meanwhile, the encoder 400 is understood to be an article that subjects the medical video to the encoding and the image quality adjustment.

Note that, the present invention is not always necessarily be carried out by using the switcher, in order to separate the transmission path of the medical video from the medical device to the monitor, from the transmission path of the medical video from the medical device to the encoder, but instead may enable the medical device per se, as the output source, to divide the medical videos to be output to the monitor and the encoder.

As explained previously, medical video system 1000 of this embodiment has the server 600 (the server in the present invention), and the viewing terminal group 700 (the viewing terminal in the present invention).

The server 600 is an article that stores the medical video having gone through the image quality adjustment and the encoding by the encoder 400.

The viewing terminal group 700 can receive streaming (either on-demand streaming or live streaming) of the medical video stored in the server 600, from the server 600.

This invention is on the premise that the display device, corresponded to the monitor group 300 and the encoder 400, is installed in an operation room, meanwhile the computer equipment, corresponded to the server 600 and the viewing terminal group 700, is installed outside of the operation room.

The present invention may, however, be carried out with at least a part of the display device, corresponded to the monitor group 300 installed outside of the operating room, or with at least a part of the computer equipment equivalent to the viewing terminal group 700 installed in the operation room.

<Operation Screen of Encoder 400>

Figure 2:
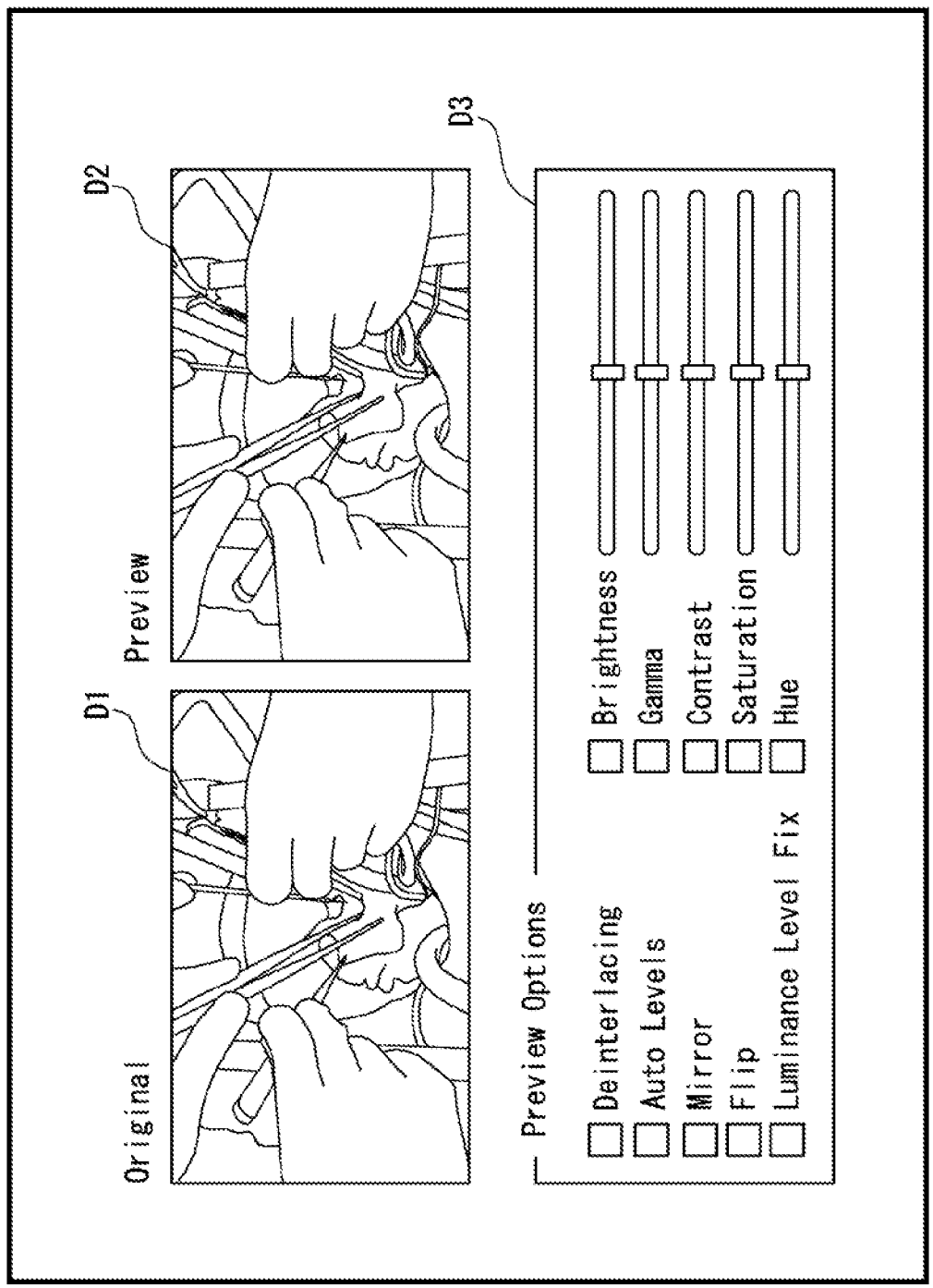
FIG. 2 is a drawing illustrating an operation screen on which the encoder is operated.

FIG. 2 is a drawing illustrating an operation screen on which the encoder is operated.

The operation screen illustrated in FIG. 2 is roughly divided into three areas: a display area D1, a display area D2, and a display area D3.

The display area D1 displays the original medical video (medical video before encoded) received by the encoder 400.

The display area D2 displays the medical video after encoded by the encoder 400.

The display area D3 displays check boxes and slide bars on which the user's operation regarding the image quality adjustment is accepted.

Note that the medical videos, displayed in the display area D1 and the display area D2 in FIG. 2 are understood to be those captured by the surgical field camera 201. Both the medical videos displayed in the display area D1 and the display area D2 are understood to be those having gone through the image quality adjustment. The description below will be based on these premises.

An operation screen illustrated in FIG. 2 is involved in image quality adjustment that can be carried out by the encoder 400, and can separately display an operation screen regarding other function (for example, recording function, playback function, or capture function).

Now " . . . can separately display an operation screen" means that the operation screen and the other operation screen may be concurrently displayed (in a temporarily overlapped manner) on the other display area different from the operation screen illustrated in FIG. 2; or means that the other operation screen may be displayed in a state changed from the state of the operation screen illustrated in FIG. 2 (in a temporarily separated manner).

The operation screen illustrated in FIG. 2 has displayed thereon (on the left side of the display area D3) the check boxes that accept the user's operation regarding the processes below.

Upon checking the check box for deinterlacing (Deinterlacing) by the user, a video being displayed in an interlaced format in the display area D1 is deinterlaced, and the deinterlaced video is displayed in the display area D1 and the display area D2.

Upon checking the check box for automatic level correction (Auto Levels) by the user, an image quality level of the input video is automatically corrected, and the corrected video is displayed in the display area D1 and the display area D2. The image quality level to be corrected here is at least one of brightness, gamma value, contrast value, saturation and hue. That is, the items to be subjected to the automatic level correction is at least a part of the items to be subjected to the image quality adjustment, which may be carried out by operating the check boxes in the right column and the slide bars in the display area D3 descried later.

Upon checking the check box for lateral inversion (Mirror) by the user, the input video is subjected to image processing for lateral inversion, and the laterally inverted video is displayed in the display area D1 and the display area D2.

Upon checking the check box for vertical inversion (Flip) by the user, the input video is subjected to image processing for vertical inversion, and the vertically inverted video is displayed in the display area D1 and the display area D2.

Upon checking the check box for luminance correction (Luminance Level Fix) by the user, the input video is subjected to automatic luminance correction, and the corrected video is displayed in the display area D1 and the display area D2. Also luminance correction in this embodiment will be explained as a part of the image quality adjustment.

The operation screen illustrated in FIG. 2 has displayed thereon (on the right side of the display area D3) the check boxes that accept the user's operation regarding the processes below.

Upon checking the check box for brightness (Brightness) by the user, a slide bar used for brightness adjustment of the input video becomes active. More specifically, rightward operation of the slide bar by the user increases the brightness, meanwhile left and operation of the slide bar by the user decreases the brightness. Upon unchecking of the check box, the slide bar becomes inactive.

Upon checking the check box for gamma value (Gamma) by the user, a slide bar used for gamma value adjustment of the input video becomes active. More specifically, rightward operation of the slide bar by the user increases the gamma value, meanwhile leftward operation of the slide bar by the user decreases the gamma value. Upon unchecking of the check box, the slide bar becomes inactive.

Upon checking the check box for contrast value (Contrast) by the user, a slide bar used for contrast value adjustment of the input video becomes active. More specifically, rightward operation of the slide bar by the user increases the contrast value, meanwhile leftward operation of the slide bar by the user decreases the contrast value. Upon unchecking of the check box, the slide bar becomes inactive.

Upon checking the check box for saturation (Saturation) by the user, a slide bar used for saturation adjustment of the input video becomes active. More specifically, rightward operation of the slide bar by the user increases the saturation, meanwhile leftward operation of the slide bar by the user decreases the saturation. Upon unchecking of the check box, the slide bar becomes inactive.

Upon checking the check box for hue (Hue) by the user, a slide bar used for hue adjustment of the input video becomes active. More specifically, rightward operation of the slide bar by the user increases the hue (making red closer to yellow, green closer to cyan, and blue closer to magenta), meanwhile leftward operation of the slide bar by the user decreases the hue (making red closer to magenta, green closer to yellow, and blue closer to cyan). Upon unchecking of the check box, the slide bar becomes inactive.

Upon adjustment of brightness, gamma value, contrast value, saturation and hue of the input video, through operation of the slide bars, the adjusted video is displayed in the display area D1 and the display area D2.

The medical video having gone through such image quality adjustment is further encoded, and recorded by the encoder 400.

Now, the recording by the encoder 400 means a process of storing the medical video, having gone through the image quality adjustment and the encoding, to some sort of storage medium. The storage medium used for storage may be a built-in storage medium in the encoder 400, or may be a storage medium that belongs to an external device of the encoder 400. Considering in the context of this embodiment, both of a process that the encoder 400 stores the medical video in the built-in storage, and a process that the server 600 stores the medical video after transferred from the encoder 400 to the server 600, are understood to be recording carried out by the encoder 400.

Now the aforementioned processes regarding the encoder 400 will be summarized.

The encoder 400 has the display area D3 in which the user's operation regarding the image quality adjustment is acceptable, wherein the display area D3 corresponds to the operation accepting unit in the present invention.

The encoder 400 functions to carry out the image quality adjustment, in response to the user's operation accepted in the display area D3, wherein this function corresponds to the image quality adjusting unit in the present invention.

The encoder 400 functions to record the medical video, having gone through the image quality adjustment and the encoding, in the built-in storage and the server 600, wherein this function corresponds to the recording unit in the present invention.

The encoder 400 has the display area D1 and the display area D2 for displaying therein the medical video having gone through the image quality adjustment curried out by the image quality adjusting unit, wherein the areas correspond to the display area in this invention.

The display area D3 is kept ready for acceptance of the user's operation, both during a recording period or non-recording period of the encoder 400.

Upon acceptance of the user's operation during recording, the recorded medical video is switched in the middle (from the time point of acceptance of the user's operation) to a video that reflects the image quality adjustment in response to the user's operation.

Meanwhile, upon acceptance of the user's operation during the non-recording period, the recorded medical video is switched from the beginning (from the time point when the recording was started) to a video that reflects the image quality adjustment in response to the user's operation.

The image quality adjustment in response to the user's operation made in the display area D3 is linearly reflected to the medical videos displayed in the display area D1 and the display area D2. Note, however, that the display area D1, aimed to display the medical video before encoded, displays the medical video both during the recording period and the non-recording period of the encoder 400. Meanwhile, the display area D2, aimed to display the medical video after encoded, displays the medical video during the recording period of the encoder 400, whereas does not display the medical video during the non-recording period.

In other words, upon acceptance of the user's operation by the display area D3 during recording by the encoder 400, the display area D1 and the display area D2 display the medical videos that reflect the image quality adjustment in response to the user's operation, from the time point of acceptance of the user's operation. As will be detailed later, the display area D2 during recording displays a medical video equivalent to the medical video just being recorded (medical video after encoded), so that the user can perform proper operation, while checking effects of the image quality adjustment seen in the display area D2. Meanwhile, the display area D1 during recording displays a medical video not yet encoded (medical video brighter than in the display area D2), but the image quality adjustment can be reflected in the same manner as in the display area D2, so that the user can check the effects of the image quality adjustment, also by viewing the display area D1.

Also in a case where the display area D3 accepts the user's operation during the non-recording period of the encoder 400, the display area D1 displays the medical video that reflects the image quality adjustment in response to the user's operation, from the time point of acceptance of the user's operation. Hence, the user can adjust the image quality of the medical video before being recorded, while checking in the display area D1. Note that the display area D2 during the non-recording period does not display the medical video.

As described previously, the encoder 400 has the display area D1 (the first display area in the present invention) that displays medical video before encoded, and the display area D2 (the second display area in the present invention) that displays the medical video after encoded.

The medical video displayed in the display area D1 is preferably synchronized with the medical video displayed in the display area D2 (videos are displayed in a time-matched manner to a degree that the user does not feel delay).

With such structure of the encoder 400, the user can adjust the image quality at will, while comparing the video in the display area D1 and the video in the display area D2. For example, the user can operate so as to make the image quality of the medical video displayed in the display area D2, closer to the image quality of the medical video having been displayed in the display area D1 before the operation.

Note however that the delay, between display of the medical video in the display area D1 and display of the medical video in the display area D2, is preferably smaller than that of display of the medical video displayed on the viewing terminal group 700, in a case where the same medical video is received by the viewing terminal group 700 by live streaming.

In other words, with reference to the time at which the medical video is displayed in the display area D1 by the encoder 400, the time at which the encoder 400 displays the medical video in the display area D2 is preferably earlier than the time at which the viewing terminal group 700 displays the medical video received from the server 600 through live streaming.

Note that the encoder 400 is not necessarily able to carry out the entire range of the aforementioned image quality adjustment, instead may only be able to carry out a part thereof (for example, at least one of brightness adjustment, gamma adjustment, contrast adjustment, saturation adjustment, or hue adjustment). The image quality adjustment carried out by the encoder 400 is not limited to those described above, instead allowing addition of any of known image quality adjustment.

Although the operation screen illustrated in FIG. 2 has been explained on the premise that the user's operation is accepted to enable image quality adjustment for the medical video received from a single input system, the encoder 400 may alternatively carry out the image quality adjustment for each of the medical videos received from a plurality of input system. The encoder 400 in this case can preferably carry out the image quality adjustment which differs for each input system. This is because the degree of optimum image quality adjustment differs for each medical video.

For embodying such modified example, also the operation screen involved in the image quality adjustment preferably has a unit that accepts the user's operation for each input system of the encoder 400.

<Process Flow of Encoder 400>

Next, a process flow of the encoder 400 will be explained.

FIG. 3 is a flow chart illustrating a process flow executed by the encoder 400.

The encoder 400 receives the medical video from the switcher 100 (step S102), decodes the received medical video (step S104), writes the decoded video data to a memory (step S106), subjects the video data to image quality adjustment (step S110), and then advances to processes in step S112 and step S114.

Note that the process in step S110 is at least one process of the image quality adjustment made in the display area D3 in response to the user's operation, or may be combination of two or more processes.

The encoder 400 displays, in the display area D1, the video data having gone through the image quality adjustment (step S112). The process flow thus comes to the end.

The encoder 400 also carries out the process below, concurrently with the process in step S112.

The encoder 400 encodes the video data having gone through the image quality adjustment, writes the encoded video data in the memory (step S114), and advances to the processes in step S116 and step S120.

The encoder 400 decodes the video data having gone through the image quality adjustment and the encoding (step S116), and displays the video data in the display area D2 (step S118). The process flow thus comes to the end.

The encoder 400 exports the video data having gone through the image quality adjustment and the encoding to a built-in storage of the encoder 400 (step S120), concurrently with the processes in step S116 and step S118, and transfers the video data thus exported to the storage to the server 600 (step S122). The process flow thus comes to the end.

Note that the video data transferred to the server 600, intended to be streamed on-demand, is delivered on demand by the viewing terminal group 700 after stored (recorded) in the server 600. Meanwhile, when the video data transferred to the server 600 is live-streamed, the video data is stored (recorded) in the server 600, as well as sequentially distributed to the viewing terminal group 700.

Since the encoder 400 concurrently carries out the process of displaying the medical video in the display area D1, the process of displaying the medical video in the display area D2, and exports the medical video having gone through the image quality adjustment and the encoding to the storage (the medical video is displayed in the display area D2, before finishing export to the server 600), so that time lag would not occur between the display area D1 and the display area D2 (the delay would only be not recognizable by the user).

With such processing by the encoder 400, the live streaming from the server 600 can minimize the delay (time lag from the display in the display area D1) that possibly occurs in the viewing terminal group 700.

Note that the process flow illustrated in FIG. 3 is merely an illustrative one, allowing modifications in the individual processes, omission of a part of the illustrated processes, or addition of other unillustrated process, so long as the purpose of the present invention can be achieved.

For example, although FIG. 3 has disclosed the process flow in which the image quality adjustment (step S110) is directed to both the medical video displayed in the display area D1 and the medical video displayed in the display area D2, the purpose of the present invention can be achieved alternatively by a process flow in which only the medical video displayed in the display area D2 is targeted at. In this modified example, either the image quality adjustment or the encoding may come first, or both may be carried out after combined into one process.

This embodiment also encompasses technical spirits below.

(1) A medical video processing system that processes medical video produced by a medical device, the system comprising:

a monitor accepting the medical video input through a first transmission path, and displaying thereon the input medical video; and an encoder accepting the medical video through a second transmission path which is different from the first transmission path, and subjecting the input medical video to encoding, and the encoder subjecting the input medical video to image quality adjustment.

(2) The medical video processing system according to (1), wherein the encoder having:

an operation accepting unit capable of accepting a user's operation for the image quality adjustment;

an image quality adjusting unit that takes part in the image quality adjustment, in response to the user's operation accepted by the operation accepting unit; and a recording unit that records the medical video having gone through the image quality adjustment and the encoding, and, the system being devised so that, upon acceptance of the user's operation by the operation accepting unit during recording by the recording unit, the recorded medical video is switched in the middle to a video that reflects the image quality adjustment in response to the user's operation.

(3) The medical video processing system according to (2), wherein the encoder has a display area that displays the medical video having gone through the image quality adjustment by the image quality adjusting unit, and upon acceptance of the user's operation by the operation accepting unit during recording by the recording unit, the display area displays the medical video that reflects the image quality adjustment in response to the user's operation, from the time point of acceptance of the user's operation.

(4) The medical video processing system according to (3), wherein the encoder is configured to enable display of the medical video in the display area, also during a non-recording period by the recording unit, and, upon acceptance of the user's operation by the operation accepting unit during the non-recording period by the recording unit, the display area displays the medical video that reflects the image quality adjustment in response to the user's operation, from the time point of acceptance of the user's operation.

(5) The medical video processing system according to (3) or (4), wherein the display area has a first display area that displays the medical video before encoded, and a second display area that displays the medical video after encoded.

(6) The medical video processing system according to (5), further having:

a server that receives, and then stores therein, the medical video having gone through the image quality adjustment and the encoding from the encoder; and a viewing terminal capable of receiving, from the server, live streaming of the medical video stored in the server, and, the system is devised so that, with reference to the time at which the encoder displays the medical video in the first display area, the time at which the encoder displays the medical video in the second display area comes earlier than the time at which the viewing terminal displays the medical video by live streaming.

(7) The medical video processing system according to any one of (1) to (6), wherein the image quality adjustment carried out by the encoder includes at least one of brightness adjustment, gamma adjustment, contrast adjustment, saturation adjustment, or hue adjustment.

(8) An encoder used for the medical video processing system described in any one of (1) to (7).

This application claims priority to Japanese Patent Application No. 2020-018659 filed on Feb. 6, 2020, the entire contents of which are incorporated by reference herein.

REFERENCE SIGNS LIST 1000 medical video system
100 switcher
200 medical device group
201 surgical field camera
202 head mount camera
203 electronic medical chart device
204 bioinstrument
205 endoscope
206 microscope
207 ultrasonograph
208 fluoroscope
300 monitor group
400 encoder
500 network
600 server
700 viewing terminal group
D1, D2, D3 display area The invention claimd is:

1. A medical video processing system that processes medical video produced by a medical device, the system comprising:

a monitor accepting the medical video input through a first transmission path, and displaying thereon the input medical video; and an encoder accepting the medical video through a second transmission path which is different from the first transmission path, and subjecting the input medical video to encoding and image quality adjustment, the encoder comprising:

an operation accepting unit capable of accepting a user's operation for the image quality adjustment;

an image quality adjusting unit that takes part in the image quality adjustment, in response to the user's operation accepted by the operation accepting unit;

a recording unit that records the medical video having gone through the image quality adjustment and the encoding; and a first display area that displays the medical video having gone through the image quality adjustment, but not through the encoding, and, the system being devised so that, upon acceptance of the user's operation by the operation accepting unit during recording by the recording unit, the medical video to be displayed in the first display area is switched to a video that reflects the image quality adjustment in response to the user's operation, from the time point of acceptance of the user's operation.

2. The medical video processing system according to claim 1, wherein the encoder further comprises a second display area that displays the medical video having gone through the image quality adjustment and the encoding, and, the system is devised so that, upon acceptance of the user's operation by the operation accepting unit during recording by the recording unit, both the medical video to be displayed in the first display area and the medical video to be displayed in the second display area are switched to videos that reflect the image quality adjustment in response to the user's operation, from the time point of acceptance of the user's operation.

3. The medical video processing system according to claim 2, further comprising:

a server that receives, and then stores therein, the medical video having gone through the image quality adjustment and the encoding from the encoder; and a viewing terminal capable of receiving, from the server, live streaming of the medical video stored in the server, and, the system is devised so that, with reference to the time at which the encoder displays the medical video in the first display area, the time at which the encoder displays the medical video in the second display area conies earlier than the time at which the viewing terminal displays the medical video by live streaming.

4. The medical video processing system according to claim 1, wherein the image quality adjustment carried out by the encoder includes at least one of brightness adjustment, gamma adjustment, contrast adjustment, saturation adjustment or hue adjustment.

5. An encoder used for the medical video processing system described in claim 1.

* * * * *